United States Patent
Chen et al.

(10) Patent No.: US 11,370,725 B2
(45) Date of Patent: Jun. 28, 2022

(54) OXY-FUEL CRACKING FURNACES AND BOILERS USING CO2 AS THE WORKING FLUID

(71) Applicant: Lamar University, Beaumont, TX (US)

(72) Inventors: Daniel H. Chen, Beaumont, TX (US); Russel Buss, Beaumont, TX (US); Dan P. Fernandes, Beaumont, TX (US)

(73) Assignee: Lamar University, a Component of the Texas State University System, an Agency of the State of Texas, Beaumont, TX (US)

( * ) Notice: Subject to any disclaimer, the term of this patent is extended or adjusted under 35 U.S.C. 154(b) by 0 days.

(21) Appl. No.: 17/388,870

(22) Filed: Jul. 29, 2021

(65) Prior Publication Data

US 2022/0033324 A1 Feb. 3, 2022

Related U.S. Application Data

(60) Provisional application No. 63/058,641, filed on Jul. 30, 2020.

(51) Int. Cl.
*B01J 6/00* (2006.01)
*C07C 4/02* (2006.01)

(52) U.S. Cl.
CPC ............... *C07C 4/025* (2013.01); *B01J 6/00* (2013.01)

(58) Field of Classification Search
CPC ................... C07C 4/025; B01J 6/00
See application file for complete search history.

(56) References Cited

U.S. PATENT DOCUMENTS

2011/0250119 A1* 10/2011 Mello .................. C01B 3/34
564/69

\* cited by examiner

*Primary Examiner* — Thuan D Dang
(74) *Attorney, Agent, or Firm* — Kowert, Hood, Munyon, Rankin & Goetzel, P.C.; Gareth M. Sampson

(57) ABSTRACT

Disclosed is an ethylene and/or propylene cracker unit that uses recycled carbon dioxide as a working fluid. A boiler may also use recycled carbon dioxide as a working fluid. In either instance, instead of releasing high-purity $CO_2$ into the atmosphere, the bulk of the $CO_2$ is utilized as the working fluid and the produced $CO_2$ is captured and sent to the pipeline for utilization or storage. These systems will minimize heat loss and achieve essentially zero $CO_2$ emission to the air.

14 Claims, 5 Drawing Sheets

OXY-FUEL CRACKING FURNACES AND BOILERS USING CO2 AS THE WORKING FLUID

PRIORITY CLAIM

This patent application claims priority to U.S. Provisional Patent Application No. 63/058,641 filed Jul. 30, 2020, which is incorporated by reference as if fully set forth herein.

BACKGROUND OF THE INVENTION

1. Field of the Invention

The invention generally relates to the formation of ethylene and/or propylene from hydrocarbon feedstocks.

2. Description of the Relevant Art

Ethylene and propylene are major petrochemicals as they are a primary building block to produce many other chemicals and products. Ethylene and propylene are produced from a variety of hydrocarbon feedstocks using cracking or pyrolysis in a furnace commonly referred to as a "cracker." Common hydrocarbon feedstocks of steam cracking are the ethane/propane derived from natural/associated gas, naphtha, and other hydrocarbons.

Cracking or pyrolysis is a reaction in the gas phase at high temperatures (e.g., above 800° C. such as 840° C. to 890° C.). During a cracking process, gaseous hydrocarbons (typically, ethane, or propane) are treated with steam at high temperatures. Under these conditions the hydrocarbons in the feed stream are converted into ethylene and/or propylene plus hydrogen by various free radical or molecular reaction schemes. In a typical cracking process, the steam to hydrocarbon ratio is 0.3-0.5. Dilution steam is supplied to the furnace area of the cracker at elevated temperature and pressure (e.g., 7 bar and 190° C.). The dilution steam has a dual function of lowering the hydrocarbon partial pressure and reducing the coking rate in the radiant coils.

Temperature along with reactor pressure and steam-hydrocarbon ratio are the critical parameters in cracking operations. Cracking can be represented by free radical or molecular reaction schemes. The COT (coil outlet temperature) is an important indicator for severity to avoid over or under cracking.

Cracking, however, produces large amounts of greenhouse gases and other pollutants such as NOx. The recently released report "The Fourth National Climate Assessment" by the U.S. government on the National Oceanic and Atmospheric Administration website highlights that climate change is real and global warming will increase in the future which will threaten the health and wellbeing of the world populations. Global warming will further increase the economic costs to countries due to an increasing number of natural disasters in the future.

The rise in the global emissions of carbon dioxide was at 2.7 percent in 2018. This expected increase, would bring fossil fuel and industrial emissions to a record high of 37.1 billion tons of carbon dioxide per year. The US, China, and India will account for 2.5 percent, 5 percent, and 6 percent growth of emissions respectively.

According to the UN-backed scientific panel, nations have barely a decade left to take unprecedented actions to cut emissions in half by 2030 to keep the Earth's warming below 1.5 degrees Celsius or suffer the consequences of climate change. A global economy which is growing at a fast pace coupled with the accelerated development in nations like China and India, which are heavily reliant on coal for power production, will inevitably stoke more global emissions of carbon dioxide. Coal accounts for 60 percent of electricity production in China. The availability of cheap feedstock of natural gas in the U.S., will warrant the construction of ethane crackers in the U.S. According to the American Chemistry Council, $200 billion will be invested on new ethane cracker facilities to take advantage of the cheap availability of natural gas in the U.S.

BRIEF DESCRIPTION OF THE DRAWINGS

Advantages of the present invention will become apparent to those skilled in the art with the benefit of the following detailed description of embodiments and upon reference to the accompanying drawings in which.

Figure 1A:
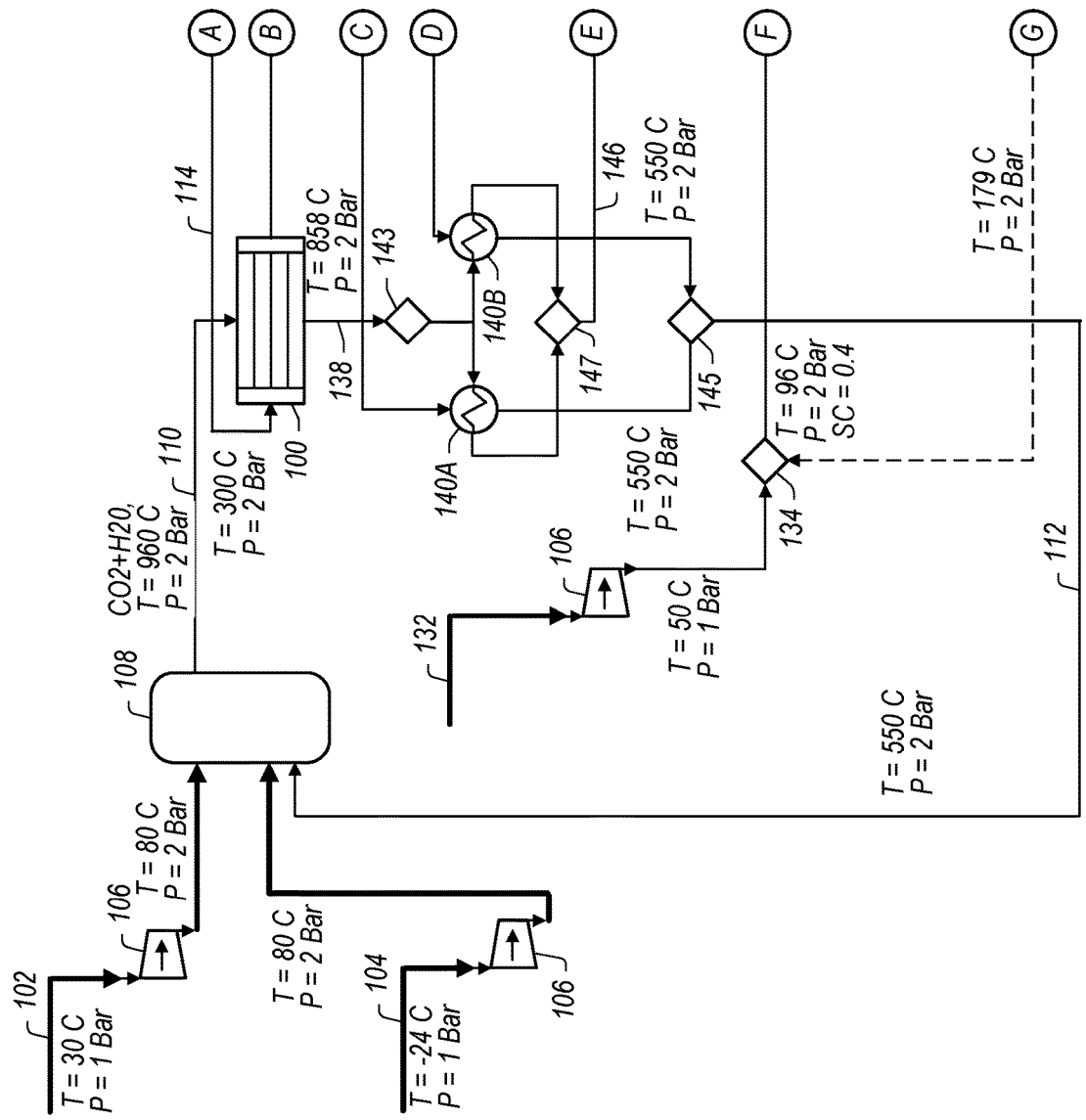
FIGS. 1A and 1B depict a process flow diagram for an ethylene and/or propylene cracker unit, according to some embodiments.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims.

DETAILED DESCRIPTION

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Furnace with $CO_2$ Recycle

Figure 1B:
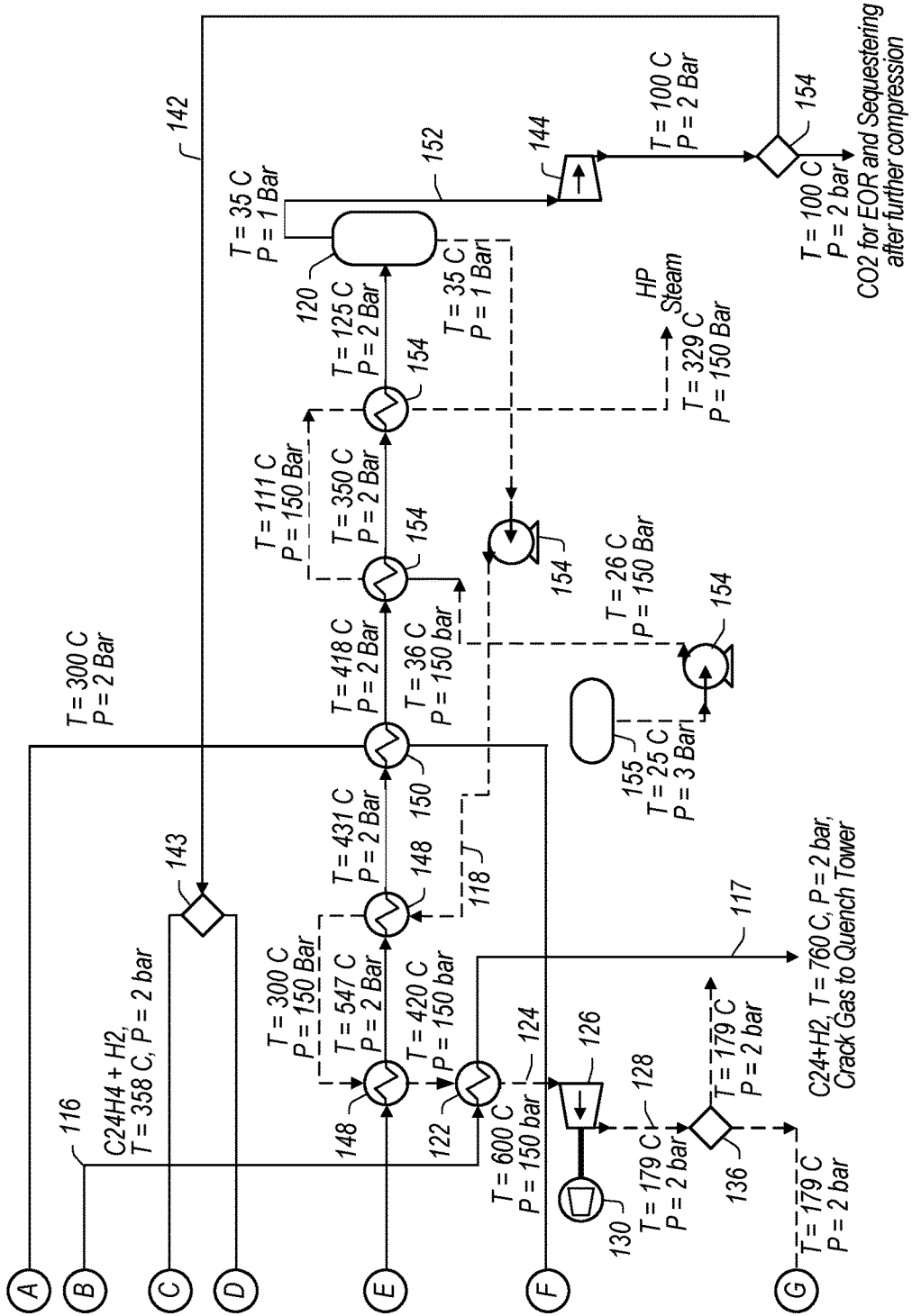

FIGS. 1A and 1B depict a process flow diagram for an ethylene and/or propylene cracker unit, according to some embodiments. Cracker unit 100 may work as a convection furnace, like a steam boiler. Cracker unit 100 may be, for example, a radiant coil cracker unit. In the illustrated embodiment, natural gas 102 and oxygen 104 are provided through compressors 106 to combustion chamber 108. Oxy-fuel combustion occurs in combustion chamber 108 to produce heated $CO_2$ gas stream 110, which supplies the heat for the cracking reaction in cracker unit 100.

In various embodiments, after cracking is finished, carbon dioxide 112 is recycled to the combustion chamber 108. Thus, instead of releasing high-purity $CO_2$ into the atmosphere, the $CO_2$ is retained in the system and utilized as the working fluid. In the illustrated embodiment, an ethylene cracker or boiler utilizes regenerative or other heat exchange media and recycled hot $CO_2$ to minimize heat loss and to achieve substantially zero $CO_2$ emission to the air. The hot cracked gas product stream (gaseous ethylene and/or propylene) may be used to heat up the ceramic media or other heat exchange media and to serve as the quench step for the furnace/boiler effluent.

Various typical operating conditions of the illustrated embodiment are described as follows. Piped natural gas 102 at 2 bar is supplied to combustion chamber 108 (shell side of ethane cracker) at 250° C. Oxygen 104 from an air separation unit (ASU) at 99.4% purity is supplied at 2 bar and 200° C. In the presence of circulated carbon dioxide 112 at 2 bar and 550° C., natural gas 102 is combusted with oxygen 104 in combustion chamber 108. The products of combustion are water and carbon dioxide 110. The recycled carbon dioxide is added to maintain the adiabatic flame temperature in an acceptable range. The heat of combustion is transferred to cracker unit 100. In cracker unit 100, ethane and steam mixture 114 is flowing through the coils at an s/c ratio of about 0.4. In a specific embodiment, the coil reactor has 48 tubes with a length of 10.5 m and an inner diameter of 0.085 m for each tube. Other configurations and dimensions are possible, depending on the amount of material being processed. In the illustrated embodiment, the maximum operating pressure is 2 bar. Cracked gas 116 leaving cracker unit 100 has the COT at 856° C. and a pressure of 2 bar. The ethylene produced is about 52% by weight. The cracked gas 116 heats up the saturated steam to superheated steam in superheater 122, which is then fed into steam turbine 126 to generate lower pressure steam 128 at 2 bar. In some embodiments, the cracked gas 116 exits the process and is provided to a quench tower at 117. The power generated by steam turbine 126 is, in one embodiment, 0.67 MW, which is sufficient to power at least some of the equipment of the plant (e.g., using electric generator 130). In some embodiments, low-pressure steam 128 is combined with hydrocarbon feed 132 (e.g., ethane) at mix valve 134 and the resulting mixture fed to cracker unit 100 as ethane and steam mixture 114. The remaining low-pressure steam 128 can be used in the plant for steam tracing of lines or exported elsewhere at valve 136.

In certain embodiments, after giving the heat for the endothermic reaction to cracker unit 100, combusted gas 138 from the cracker unit is fed to a double-bed ceramic heat exchanger media 140 by split valve 143. The double-bed ceramic heat exchange includes first heat exchange 140A in a regenerative mode and second heat exchanger 140B in a heating mode. The double-bed ceramic heat exchanger 140 is used to preheat the incoming $CO_2$ 142 (which is split by valve 143) from the $CO_2$ compressor 144 before the $CO_2$ is fed to the combustion chamber 108 as circulated carbon dioxide 112 through valve 145. The combusted gas stream 146 may leave the double-bed ceramic heat exchanger 140 through valve 147 to further exchange heat with water 118 in steam boiler 148 to generate high pressure steam and heats up the ethane and steam mix in another heat exchanger from 150 to 300° C.

The combusted gas stream 146 is then fed to separator 120 (e.g., at atmospheric pressure and temperature) where water 118 is separated from carbon dioxide 152. Separator 120 may be, for example, a knockout drum or condenser. The water 118 from the separator 120 is fed to boiler feed water pump 154, which pumps it at a high pressure (e.g., 100-150 bar) to the steam boiler 148. Extra high pressure steam can be generated by feeding water from a deaerator 155 via the pumps 154 to the HP boilers to generate steam. The carbon dioxide 152 is compressed in $CO_2$ compressor 144 to 2 bar and a temperature of 100° C. 97% of this high purity $CO_2$ is recycled back to cracker unit 100 as $CO_2$ 142, the remaining 3% $CO_2$ 154 (e.g., 3 tons/hour) must be purged to maintain the mass balance of the system. This carbon dioxide 154 can be compressed to above 74 bar pressure and cooled to ~32° C. to be in a supercritical state for export in pipelines to EOR/sequestration. The method of ethylene production in ethane crackers by recycling $CO_2$, shown in FIGS. 1A and 1B, minimizes carbon emission compared to conventional cracking processes.

Alternative Embodiments with Molecular Sieve Packed Beds

Figure 2:
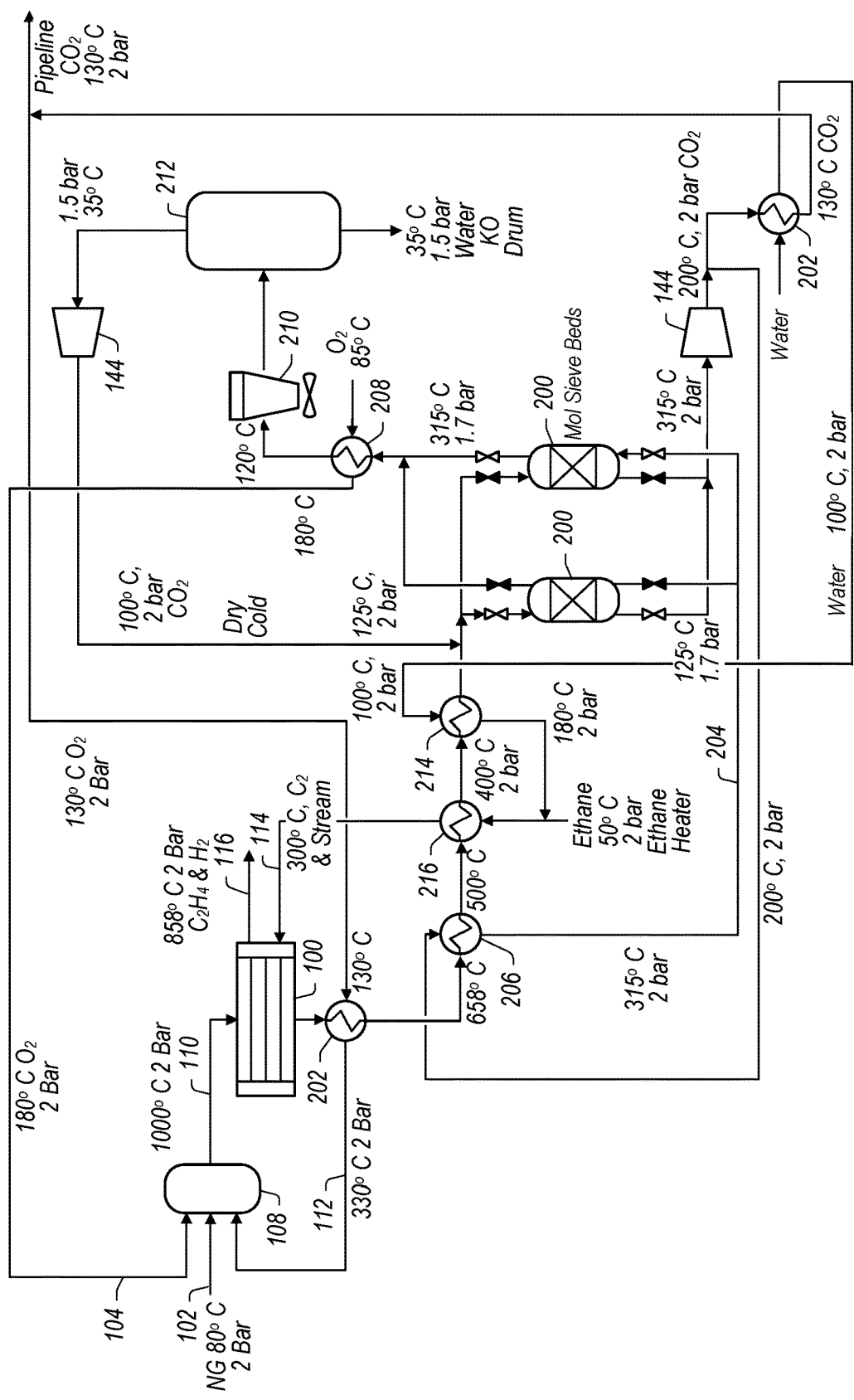
FIG. 2 depicts a process flow diagram for an ethylene and/or propylene cracker unit employing two molecular sieve packed beds, according to some embodiments.

In various embodiments, a solid desiccant may be used to remove water at elevated temperatures and warmer $CO_2$ is recycled back to the combustion chamber. FIG. 2 depicts a process flow diagram for an ethylene and/or propylene cracker unit employing two molecular sieve packed beds, according to some embodiments. In the illustrated embodiment, two beds 200 are implemented in the process to adsorb water at 125° C. The warmer dry $CO_2$ 112 may then be recycled through a series of heat exchangers 202 back to combustion chamber 108.

In some embodiments, the saturated molecular sieve beds 200 are regenerated by slip stream 204 (~10%) of the dry $CO_2$ at 315° C. coming from regenerating $CO_2$ heater 206. Then, after heat integration in heater 208 (e.g., to heat up oxygen or natural gas fuel to the combustor), the water in the cooled slip stream (e.g., cooled by cooler 210) is removed in separator 212 (e.g., a knockout drum or condenser) at ambient temperatures. The dry slip stream 214 is fed back to join the main combustion exhaust stream right before the adsorption molecular sieve bed 200, as shown in FIG. 2. In various embodiments, ethane and steam mixture 114 (e.g., feed for cracker unit 100) is generated by mixing steam from steam generator 214 and hot ethane after passing ethane heater 216.

In the illustrated embodiment, the energy saving (natural gas needed for oxy-combustion) can be estimated as the enthalpy difference between 125° C. and 35° C. (~83 kJ/kg) for 90% of the wet $CO_2$ stream that is recycled back to the combustion chamber. Note that the fraction of the dry $CO_2$ sent to the pipeline is relatively small compared to recycle $CO_2$ (~0.3%:97%). The energy penalty for compression $CO_2$ for 0.3 bar pressure drop (based on 4 A Mol Sieve Grace, 4-8 mesh beads) across the packed beds is estimated to be ~32 kJ/kg with 70% adiabatic efficiency. So the benefits outweighs the penalty for this arrangement.

It should also be noted that the configuration shown in FIG. 2 may further be optimized in terms of the desiccant used, adsorption/regeneration temperatures, and pressure drops across the packed beds. The packed beds may have other contemplated embodiments as well. For instance, a 2+1 bed vessel arrangement (2 vessels are running while 1 vessel is regenerating) may be implemented instead of the 1+1 vessel arrangement shown in FIG. 2.

Boiler with $CO_2$ Recycle

Figure 3:
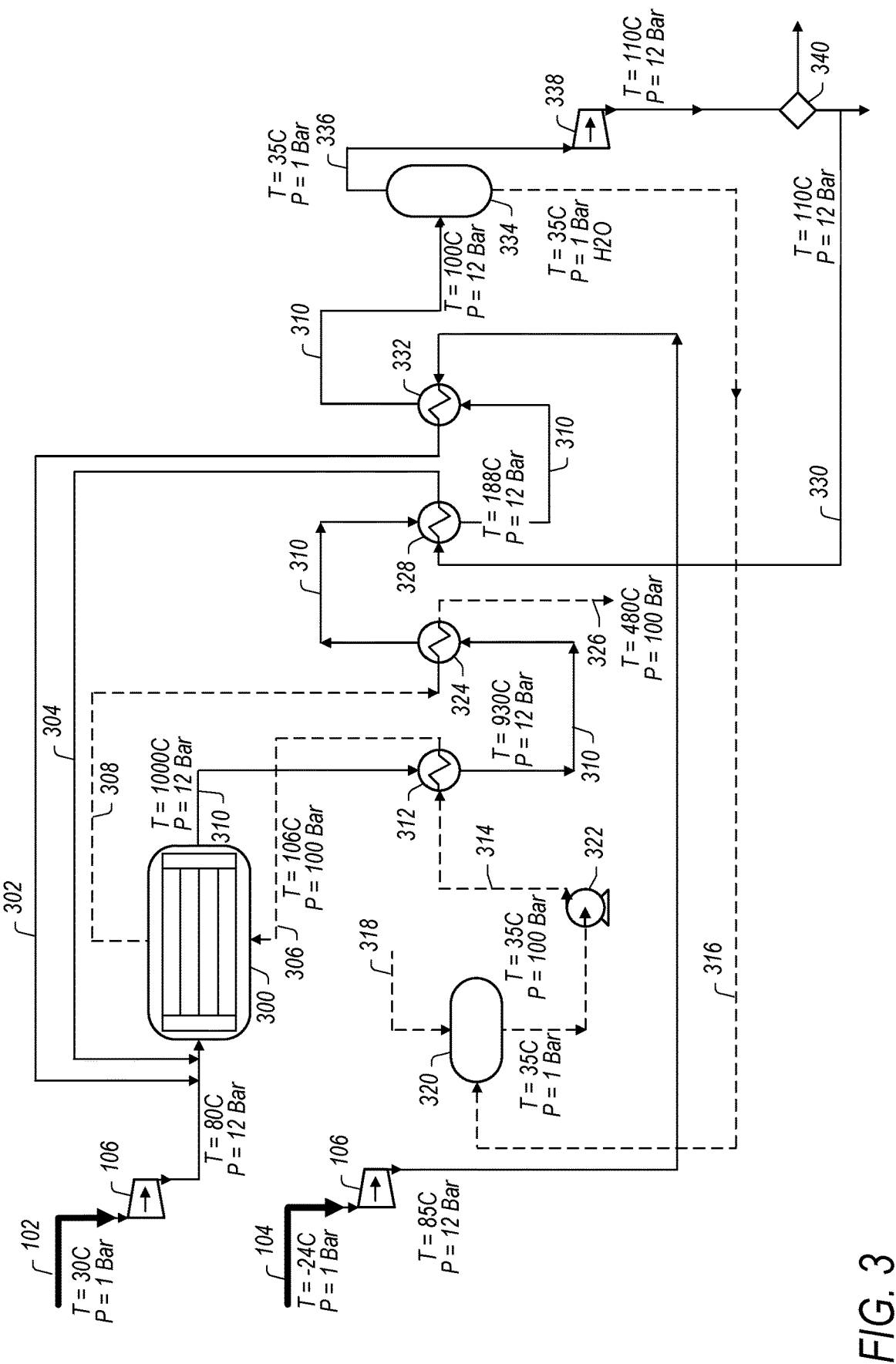
FIG. 3 depicts a process flow diagram for a boiler unit, according to some embodiments.

Principles from the cracker unit of FIGS. 1A and 1B may also be applied to a boiler operation by replacing the cracker section with a boiler. FIG. 3 depicts a process flow diagram for a boiler unit, according to some embodiments. In the illustrated embodiment, natural gas 102 is fed to boiler drum 300. In some embodiments, natural gas 102 is mixed with hot oxygen 302 and hot $CO_2$ recycle 304 for combustion in the boiler burner. Hot water 306 may also be fed to boiler with high pressure saturated steam 308 exiting the boiler. Exhaust 310 from boiler 300 may be fed to heater 312, which heats water feed 314 to hot water 306. Water feed 314 may include water recycle 316 and/or make up water 318 stored in water drum/deaerator 320 and fed by pump 322.

Exhaust 310 may pass through heater 312 to superheater 324. Superheater 324 heats high pressure steam 308 to form superheated high pressure steam 326. Exhaust 310 may then pass to $CO_2$ heater 328, which heats recycled $CO_2$ 330 to hot $CO_2$ recycle 304. Exhaust 310 then passes to oxygen heater 332, which heats oxygen 104 to hot oxygen 302. Exhaust then enters separator 334 (e.g., a knockout drum or condenser) to generate water recycle 316 and $CO_2$ 336. $CO_2$ 336 is then fed to compressor 338 and then is recycled or sent for enhanced oil recovery, sequestering, or export at valve 340.

Alternative Embodiments with Molecular Sieve Packed Beds

Figure 4:
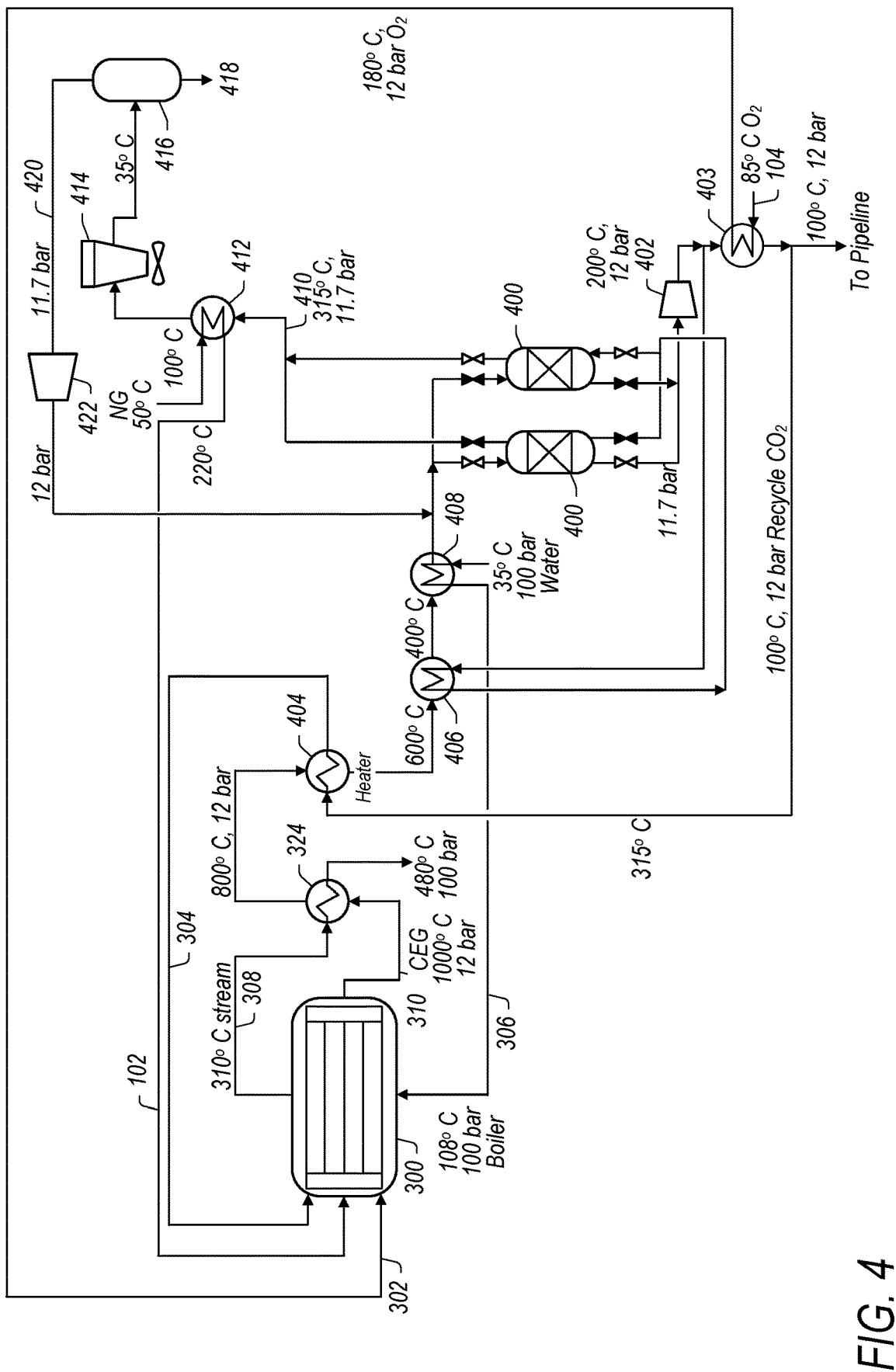
FIG. 4 depicts a process flow diagram for a boiler unit employing two molecular sieve packed beds, according to some embodiments.

As with the cracker unit, various embodiments may be contemplated with a solid desiccant being used to remove water at elevated temperatures and warmer $CO_2$ is recycled back to the boiler. The solid desiccant may include, for example, a molecular sieve, silica gel, and activated alumina to dehydrate the water containing $CO_2$ stream at elevated temperatures in lieu of a condenser operated at ambient temperatures. FIG. 4 depicts a process flow diagram for a boiler unit employing two molecular sieve packed beds, according to some embodiments. In the illustrated embodiment, two beds 400 are implemented in the process to adsorb water at 125° C. The warmer dry $CO_2$ may then be recycled through compressor 402, oxygen heater 403, and heater 404 back to boiler 300 as hot $CO_2$ 304. Oxygen heater 403 heats oxygen 104 to hot oxygen 302 for boiler 300.

Exhaust 310 goes through superheater 324 and recycle $CO_2$ heater 404 before entering regenerating $CO_2$ heater 406 and water heater 408. Exit feed 410 from beds 400 passes through natural gas heater 412 and then to cooler 414. The exit feed 410 then goes to separator 416 (e.g., a knockout drum or condenser) that produces water 418 and $CO_2$ recycle 420. $CO_2$ recycle 420 may be pressurized by compressor 422 and sent back to combine with the feed for beds 400. A slip stream (~-10% of the dry $CO_2$) is first heated by regenerating $CO_2$ heater 406, then is used to regenerate a mol sieve bed 400, the wet effluent 410 then passes through the natural gas heater 412 to pre-heat the natural gas stream 102 to the combustor. The wet $CO_2$ stream then is then cooled off by an air cooler 414 before entering the knockout drum 416. The cold dry $CO_2$ 420 passes through a compressor 422 before rejoining the combustion exhaust gas (CEG) stream.

Again, the energy saving for the boiler may be estimated as the enthalpy change from 35° C. to 125° C. (~83 kJ/kg) for 90% of the wet $CO_2$ stream that is recycled back to the boiler. Note that the fraction of the dry $CO_2$ sent to the pipeline is relatively small compared to recycle $CO_2$ (~3%: 97%). The energy penalty for compression of $CO_2$ for 0.3 bar pressure drop across the packed beds may be estimated to be ~32 kJ/kg with 70% adiabatic efficiency. Therefore, the benefit outweighs the penalty for this arrangement, as with the arrangement in FIG. 2. Additional optimizations, such as those described with respect to FIG. 2, may be added to FIG. 4.

Improvements Over the Existing Methods

Current steam cracking furnaces all emit $CO_2$ and NOx to the atmosphere. The recycled $CO_2$ furnaces are operated at the same pressure of cracking which takes place in the coils of the cracker. Further, using pure oxygen as the oxidizer in furnaces results in no nitrogen oxides (NOx) emission. The net $CO_2$ exported is of high-purity pipeline grade. Some advantages include:

(1) The application of circulating $CO_2$ concept to ethane/propane cracking furnaces to produce ethylene/propylene reduces $CO_2$ emissions.

(2) At the same time, integrating the furnace exhaust heat for preheating, steam generation, or power generation (running a turbine) reduces energy consumption of the cracking system.

(3) At the minimum natural gas (NG) consumption, the cracking system will have the lowest carbon footprint.

(4) The same circulating $CO_2$ concept can be extended to steam boiler to generate steam with $CO_2$ production for EOR or other $CO_2$ utilization purposes (e.g., urea, baking soda, or polycarbonate).

(5) A facility-wide $CO_2$ pipeline network to deliver $CO_2$ as a working gas for major combustion units such as furnaces, boilers, and heaters without greenhouse and NOx emissions.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for cracking hydrocarbons, comprising:
    a combustion chamber configured to produce a heated outlet gas from combustion of a hydrocarbon fuel source mixed with an oxidant source and carbon dioxide gas, wherein the heated outlet gas includes carbon dioxide and water;
    a cracking system configured to heat a mixture of the heated outlet gas with a hydrocarbon feed and steam to produce an ethylene and/or propylene containing stream and a separate water/carbon dioxide stream;
    a separator system configured to separate the water from the carbon dioxide in the water/carbon dioxide stream; and
    a recycling stream exiting the separator system, the recycling stream configured to recycle at least a portion of the separated carbon dioxide back to the combustion chamber.

2. The system of claim 1, further comprising a heat exchanger coupled to the recycling stream, the heat exchanger being configured to heat the recycled portion of the separated carbon dioxide stream with heat from the water/carbon dioxide stream exiting the cracking system.

3. The system of claim 1, further comprising a heat exchanger coupled to the recycling stream, the heat exchanger being configured to heat at least a portion of hydrocarbon feed with heat from the water/carbon dioxide stream exiting the cracking system.

4. The system of claim 1, further comprising one or more heat exchangers configured to generate steam coupled to cracking system.

5. The system of claim 1, wherein the separator system includes one or more molecular sieve beds configured to remove water from the water/carbon dioxide stream at elevated temperatures.

6. The system of claim 1, wherein the combustion chamber configured to produce the heated outlet gas from the combustion of natural gas.

7. The system of claim 4, wherein the one or more heat exchangers are configured to heat the water separated from the water/carbon dioxide stream to generate steam.

8. The system of claim 7, wherein the heat exchangers are configured to receive heat from the water/carbon dioxide stream exiting the cracking system for generating steam.

9. The system of claim 7, further comprising a steam turbine configured to generate electricity from at least some of the generated steam.

10. The system of claim 9, further comprising a superheater configured to superheat the generated steam before the steam turbine.

11. The system of claim 7, wherein at least some of the generated steam is recycled into the hydrocarbon fuel source.

12. The system of claim 1, wherein the separator system is a knockout drum.

13. The system of claim 1, wherein the separator system is a condenser.

14. The system of claim 1, wherein the cracking system includes a radiant coil cracker unit.

* * * * *